(12) United States Patent
Altman et al.

(10) Patent No.: US 9,161,833 B1
(45) Date of Patent: Oct. 20, 2015

(54) BLINK ACTUATION MECHANISM FOR A PROSTHETIC EYE

(71) Applicants: Stuart Maxwell Altman, Sebastopol, CA (US); Catherine Grace Broderick, El Segundo, CA (US); Elisma Caffrey, Novato, CA (US); Danielle Sheree Rond, Tracy, CA (US)

(72) Inventors: Stuart Maxwell Altman, Sebastopol, CA (US); Catherine Grace Broderick, El Segundo, CA (US); Elisma Caffrey, Novato, CA (US); Danielle Sheree Rond, Tracy, CA (US)

( * ) Notice: Subject to any disclaimer, the term of this patent is extended or adjusted under 35 U.S.C. 154(b) by 0 days.

(21) Appl. No.: 14/295,609

(22) Filed: Jun. 4, 2014

Related U.S. Application Data

(60) Provisional application No. 61/835,473, filed on Jun. 14, 2013.

(51) Int. Cl.
 *A61F 2/16* (2006.01)
 *A61F 2/14* (2006.01)
(52) U.S. Cl.
 CPC ...................................... *A61F 2/141* (2013.01)
(58) Field of Classification Search
 CPC ........................................................ A61F 2/141
 USPC .................. 623/6.64; 446/342, 343, 389, 392
 See application file for complete search history.

(56) References Cited

U.S. PATENT DOCUMENTS

| | | | | |
|---|---|---|---|---|
| 4,843,497 | A * | 6/1989 | Leyden | ............................ 360/79 |
| 5,900,923 | A * | 5/1999 | Prendergast et al. | ......... 351/221 |
| 7,234,989 | B2 * | 6/2007 | Maddocks et al. | ............ 446/392 |
| 2010/0136879 | A1 * | 6/2010 | Yang | .............................. 446/343 |
| 2010/0291832 | A1 * | 11/2010 | Sip | ................................ 446/392 |
| 2011/0097968 | A1 * | 4/2011 | Li et al. | ......................... 446/343 |

FOREIGN PATENT DOCUMENTS

DE 19632392 A1 * 2/1998

* cited by examiner

*Primary Examiner* — David H Willse
*Assistant Examiner* — Javier Blanco

(57) ABSTRACT

The invention relates to a mechanism that can be integrated with silicon facial prostheses used to recapitulate a natural facial appearance through biomimetic actuation. The prosthetic eye comprises a servo motor, microcontroller, battery, rotational shaft, and customized stainless steel tarsus. The tarsus mimics the natural eyelid and reinforces the silicon lid for rotational blink motion. A stainless steel clip holds the device together and polyurethane foam encases the device to allow proper fitting in the orbital cavity. The present invention fits within a model orbital cavity and the generated blink motion is tunable to match the position profile of an in vivo blink.

4 Claims, 6 Drawing Sheets

BLINK ACTUATION MECHANISM FOR A PROSTHETIC EYE

PRIORITY CLAIMS

The present application claims a priority benefit of U.S. Provisional Patent Application Ser. No. 61/835,473, filed Jun. 14, 2013, entitled "Prosthetic Eye." The foregoing disclosures are expressly incorporated herein by reference to the same extent as if set forth verbatim herein and shall be fully and completely a part of this document.

BACKGROUND OF THE INVENTION

1. Field of the Invention

The present disclosure relates to the field of prosthetic devices. More specifically, the invention relates to a prosthetic eye with a natural blink. Even more specifically, the present disclosure relates to a mechanism integrable into a prosthetic eye that effectuates a normal blink which provides a normal facial appearance for people with facial defects.

2. Description of the Related Art

Facial defects can be caused by congenital anomalies, trauma, or cancer. One possible facial defect is the loss of an eyelid or entire eye socket. The treatment is an orbital exenteration, a procedure where the eyelids and all orbital contents are removed. Eleven thousand people in the U.S. require an orbital exenteration every year. (P. Lee, Wang, C. C., & Adamis, A. P., "Ocular neovascularization: An epidemiological review," *Survey of Ophthalmology*, vol. 43, pp. 245-269, 1998.)

An orbital prosthesis can be created to protect sensitive skin against outside stimuli and to prevent an individual from being perceived as abnormal. While current orbital prostheses are able to replace absent facial anatomies with artificial eyes and eyelids, they are immobile and thus not truly lifelike. For patients who have already suffered the severe loss of facial anatomy and have undergone an orbital exenteration, many are also impacted psychologically when they are perceived as abnormal.

Orbital prostheses consisting of silicon eyelids and acrylic eyes are used to aesthetically cover a defect in the soft tissue of the orbit. These orbital prostheses are composed of medical grade silicone and methacrylates. Acrylic is implemented in the eyeball portion of the prosthetic and silicone is implemented in the area surrounding the eyeball (lids, brow) to mimic the appearance of the native facial tissue. Silicones are soft and flexible, maintain body temperature, and can be stretched to transparency. Furthermore, fine skin features such as hair and folds are easily introduced, making silicone the ideal material. The prosthetic anchorage can then be achieved through the use of adhesives.

Although these prostheses are the current gold standard in protecting sensitive skin against outside stimuli while mimicking the appearance of the healthy eye, they are immobile and at best create an appearance of facial paralysis. Facial paralysis and other forms of facial disfigurement attract attention and can lead to greater levels of anxiety, depression, maladaptive behavior, and reduced emotional well-being [1]. (Fu L, Bundy C, Sadiq S A. "Psychological distress in people with disfigurement from facial palsy," Eye (Lond). 2011; 25:1322-1326.) Orbital prosthesis that are static are not successful in fully overcoming the appearance of abnormality and reducing the associated psychological distress.

Although these types of orbital prosthesis appear lifelike, they do not have a blinking capability. Thus, individuals using the prosthesis can be perceived as abnormal as they are unable to blink with their orbital prosthesis. Because the orbital prosthesis does not blink, patients become prone to daily psychological trauma in addition to suffering from a loss of facial function. Thus, in order to improve a patient's quality of life, a prosthetic eye with a natural blink is needed to remove the perception of abnormality.

In addition, an orbital prosthesis with a blink tempo that can be controlled is needed to allow future synchronization with the contralateral eye. Further, the device should be easily integrated with current prosthesis designs during fabrication, should fit inside the orbital cavity, and should be non-invasive and safe for patient use. This will allow the patient to continue with their daily routine that they already follow with a standard prosthesis.

Finally, the improved device should be convenient for an ocularists to modify for different sized orbits so that the components in the device that depend on patient size can be fabricated and shaped to any given patient.

SUMMARY OF THE INVENTION

Accordingly, a need exists for a prosthetic eye with a natural blink. Therefore, the present disclosure consists of apparatuses and systems for a prosthetic eye with a natural blink and methods for manufacturing, adjusting and using the same.

Based on the foregoing, the apparatus consists of a hobby servo motor that is powered by a battery and controlled by a six-channel microcontroller. A 3D printed stationary shaft is epoxied onto the side of the motor opposite to the motor's output shaft and concentric with the motor's output shaft. The motor is aligned in the eye socket such that the two concentric shafts are in line with the left and right side of the eye. This leaves the bulk of the motor to extend into the posterior portion of the eye socket. The battery is posterior to the motor and the microcontroller is inferior to the motor. All of these components are held together with a laser cut, stainless steel clamp.

A metal tarsus, a laser cut piece of steel shaped to mimic the human tarsus, attaches to the motor. It is named for its resemblance to the human tarsus, a piece of fascis tissue in the eyelid that provides rigidity and allows the eye to blink. A metal tarsus, so named because it is a laser cut piece of steel that resembles the human tarsus, a piece of fascia in the eyelid that provides rigidity and allows the eyelid to blink, attaches to the motor. The first end of the tarsus has a hole that slips over the stationary shaft of the motor. The second end of the tarsus has a hole that is concentric with, and smaller than, the hole on the first end of the tarsus. A screw through the second end of the tarsus fastens the tarsus to the output shaft of the motor.

The metal tarsus supports the eyelid movement and is embedded into the inferior portion of the top prosthetic silicone eyelid. In order to ensure the tarsus remains adhered to the silicone, small slits are laser cut into the tarsus. The ends of the tarsus bend around the prosthetic eyeball and extend to the shafts.

The mechanism is controlled by positional feedback that is regulated by Pulse Width Modulation for a high resolution. The six-channel microcontroller is programmed for adjustable blink frequency and ttl programming script enables future synchronization with the contralateral eye.

The entire device is encased in polyurethane foam to protect the electronics while allowing proper fit and support in the orbital cavity. The device is coated with a layer of silicon so that it is hygienic and easy to insert for the patient.

BRIEF DESCRIPTION OF DRAWINGS

The following drawings and the associated descriptions are provided to illustrate embodiments of the present disclosure and do not limit the scope of the claims.

DETAILED DESCRIPTION OF THE PREFERRED EMBODIMENT

FIGS. 1 through 4 illustrate an exemplary embodiment of the disclosed orbital prosthesis assembly in perspective, perspective exploded and side views.

Figure 1:
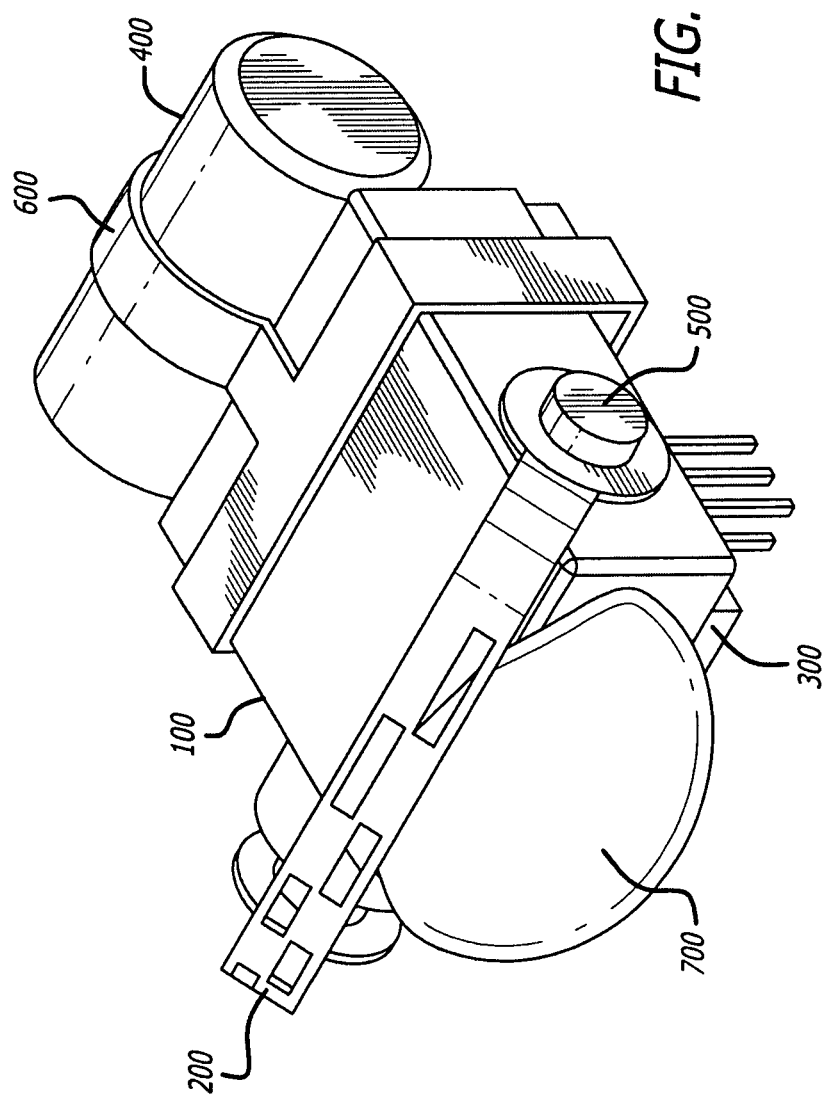
FIG. 1 is a perspective view of the orbital prosthesis with the actuated eyelid according to an embodiment of the disclosure.
Figure 2:
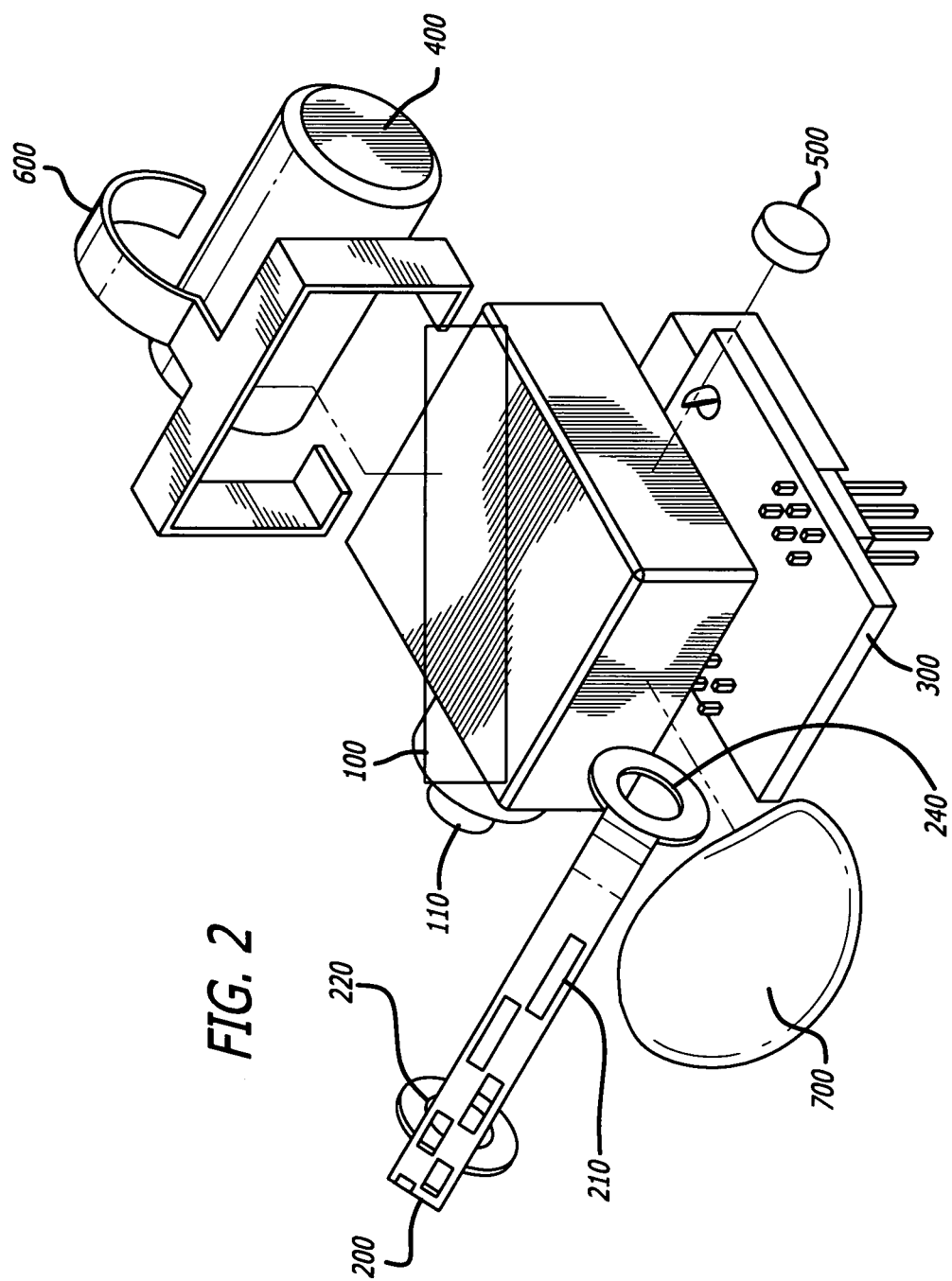
FIG. 2 is an exploded perspective view of the prosthesis shown in FIG. 1.
Figure 3:
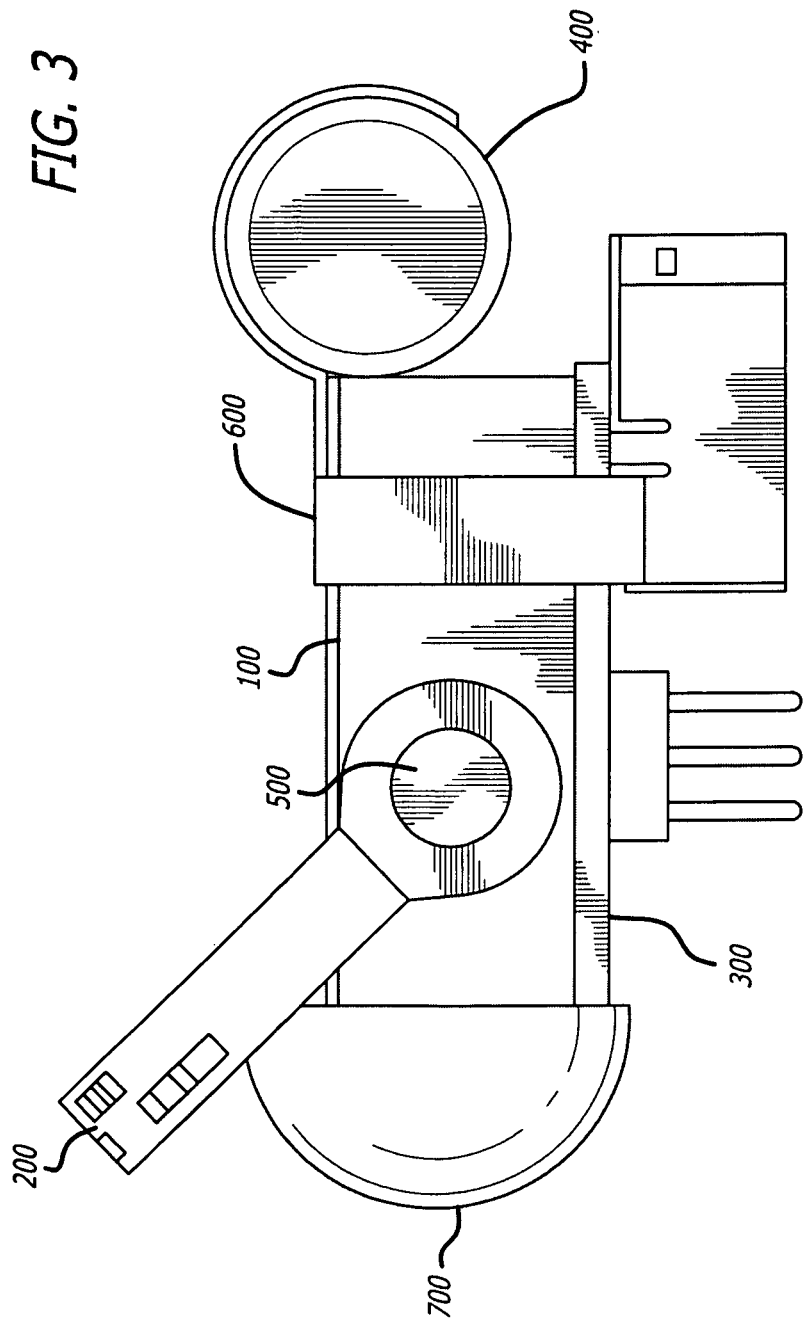
FIG. 3 is a side view of the prosthesis shown in FIG. 1.
Figure 4:
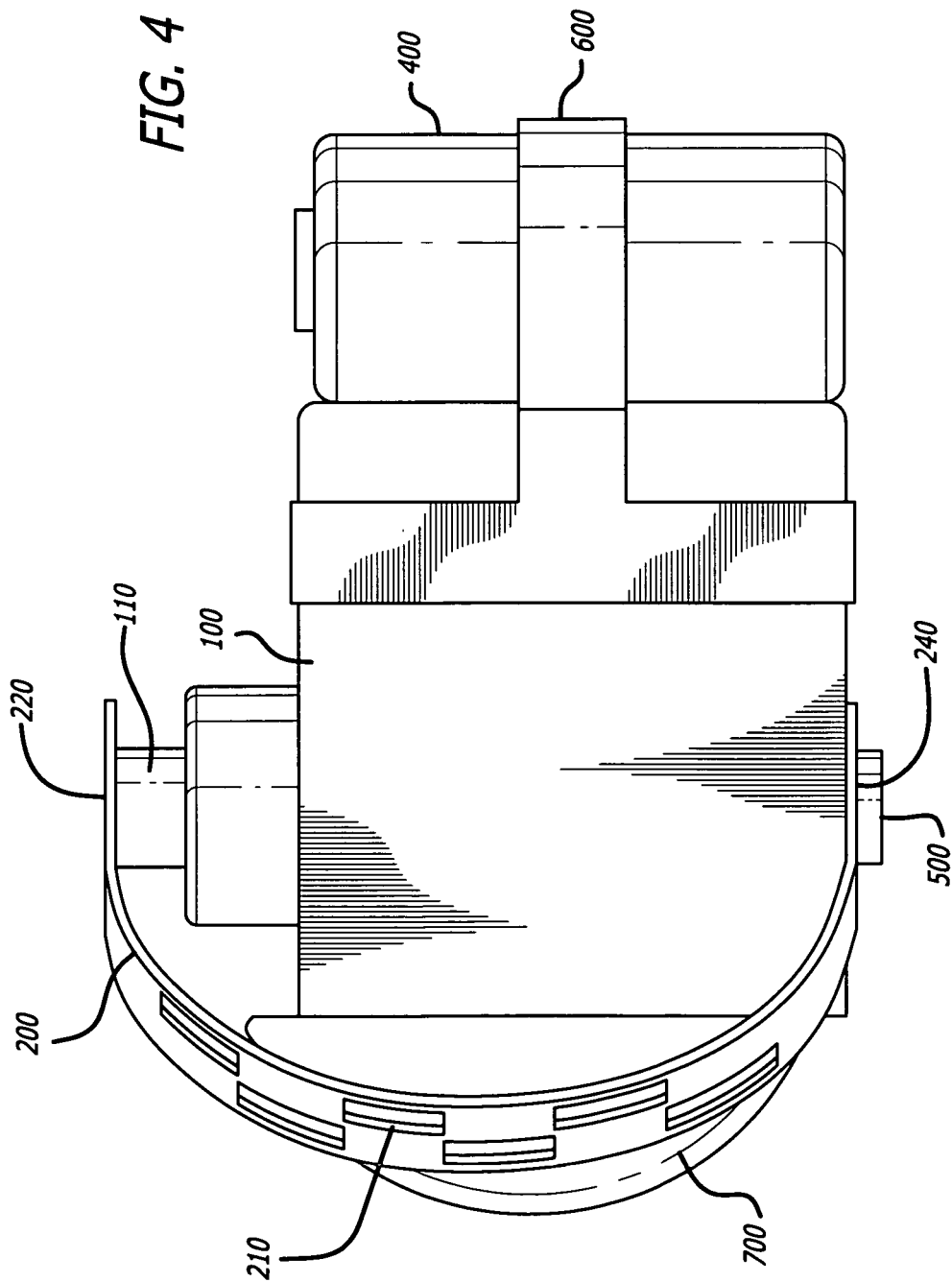
FIG. 4 is a top view of the prosthesis shown in FIG. 1.

FIG. 2 shows a perspective exploded view. The shown exemplary embodiment of the system includes a Power HD-1705MG Servo Motor 100 manufactured by Pololu, located at 920 Pilot Road, Las Vegas, Nev., 1-877-7-POLOLU, and on the Internet at www.pololu.com. The Pololu product number is 2143. One side of the Servo Motor contains an Output Shaft 110. It is important to understand that the present invention is not limited to the specific motor or type of motor disclosed since various changes and modifications may be effected herein without departing from the scope of the appended claims.

The Servo Motor 100 is connected to the stainless steel Tarsus 200 through Output Shaft 110. Stainless steel Tarsus contains Drive Hole 220 on one end of Tarsus 200. Tarsus 200 is preferably manufactured from stainless steel. A standard screw, preferably made of stainless steel, not shown in the drawings, connects Output Shaft 110 to Drive Hole 220. Tarsus 200 is named for its shape and the fascia in the human eye that it mimics. There are numerous methods to connect Shaft 110 to Drive Hole 220 and the invention is not limited to the manner of the connection. For example, Output Shaft 110 could extend through Drive Hole 220 in a press or interference fit with the diameter of Output Shaft 110 larger than the diameter of Drive Hole 220. Output Shaft 110 could also be epoxied or soldered to Tarsus 200 or Output Shaft 110 could be connected to Tarsus 200 through other mechanical means.

The shown exemplary embodiment of the system includes a Micro Maestro 6-channel Servo Controller 300 manufactured by Pololu. The Servo Controller 300 controls the actuation of Servo Motor 100. Servo Controller 300 is programmed through a scripting language. A comprehensive guide for interfacing with and programming the Servo Controller 300 is contained in the Pololu Maestro Servo Controller User's Guide, 2001-203, available from Pololu.

The Pololu Maestro Servo Controller User's Guide contains detailed instructions from the manufacturer pertaining to the Maestro program and scripting language. Servo Controller 300 is programmed via a standard general purpose computer. The Servo Controller 300 and the general purpose computer are connected via a standard and well-known in the art mini-B USB cable.

Servo Controller 300 is designed to interface with a PC operating system but the manual discloses procedures for interfacing with other operating systems. After connecting a general purpose PC computer to the Servo Controller 300 via a mini-B USB cable, the program software will automatically begin downloading and installing on the PC computer. Alternatively, the software can be downloaded free of charge from Pololu.

It is important to understand that the present invention is not limited to the type of microcontroller, including deviations in the script language or commands, since various changes and modifications may be effected herein without departing from the scope of the appended claims.

The shown exemplary embodiment of the system includes an 4Lr44 Px28A 6V alkaline Battery 400 which powers Servo Controller 300 and Servo Motor 100. This specific battery was selected based on size and economic feasibility. Many other power sources may be used with no change to the appended claims.

The shown exemplary embodiment of the system includes an Ultimaker PLA Shaft 500. Shaft 500 is fabricated using an Ultimaker 3D printer manufactured by Ultimaker B.V., Burgemeester R. vd Venlaan 11, 4191PL Geldermalsen, The Netherlands, +31 (0)345 712 017, which is located on the Internet at www.ultimaker.com. Shaft 500 is epoxied on the side of Servo Motor 100 opposite of Output Shaft 110. Shaft 500 is positioned such that it is concentric with Output Shaft 110.

Tarsus 200 contains Alignment Hole 240 on the second end of the Tarsus, away from the end with Drive Hole 220.

A silicone Eyelid 700 is bonded to Tarsus 200. Tarsus 200 contains Slits 210. Slits 210 enhance the bonding between Tarsus 200 and Eyelid 700.

Laser-cut Clip 600, preferably of stainless steel, holds the components of the device (Servo Motor 100, Tarsus 200 with attached silicone Eyelid 700, Servo Controller 300, and Alkaline Battery 400) together.

The biomimetic ocular prosthesis has a stainless steel eyelid, referred to as Tarsus 200 because it simulates this part of the eye anatomy, is used in conjunction with Servo Motor 100 in order actuate an eye blink. Servo Motor 100 is configured horizontally such that the rotating Output Shaft 110 is on one side of the eye. The Tarsus ends are fastened to the motor's Output Shaft 110 and PLA Shaft 500. The rotating motor Output Shaft 110 is fastened to the Tarsus with a stainless steel Screw 220.

The other side of the Tarsus is retained by use of a 3D printed polymer Shaft 500 that is attached to the Servo Motor with Loctite Epoxy Plaster Bonder. Shaft 500 slips through a hole in the side of the Tarsus so as to prevent the Tarsus and attached silicone Eyelid 700 from moving along the x, y, and z-axis, while maintaining angular rotation about the Shaft 500. The acrylic Eye (part of the current prosthesis) is affixed to the Long Edge 120 of Servo Motor 100. The components are held together using a laser cut stainless steel Clip 600 that encloses the Servo Controller 300, Servo Motor 100, and Battery 400. Polyurethane foam, not shown, encases the components and serves to insulate the device and provide comfort to the patient. The entire device can then be enclosed in silicone for easy insertion and removal by the patient.

Servo Motor 100 provides positional feedback and is regulated by pulse width modulation for a high angular and temporal resolution. Servo Motor 100 attaches to Tarsus 200 that is used to reinforce silicone Eyelid 700 for a rotational blink motion. Servo Controller 300 is programmed for adjustable blink frequency and ttl script enables future synchronization with the contralateral eye. Clip 600 holds the device together and polyurethane foam encases the device to protect the electronics while allowing proper fit and support in the orbital cavity. A layer of silicon coats the device so that it is hygienic and easy to insert for the patient.

The assembled device fits into a facial mold of an average orbit. During actuation, the prosthetic eye blink was recorded and compared with literature values of an average in vivo blink. P. A. Federspil, "Implant-retained craniofacial prostheses for facial defects," *GMS Curr Top Otorhinolaryngol Head Neck Surg.*, vol. 8, p. Doc03, 2009.

Figure 5:
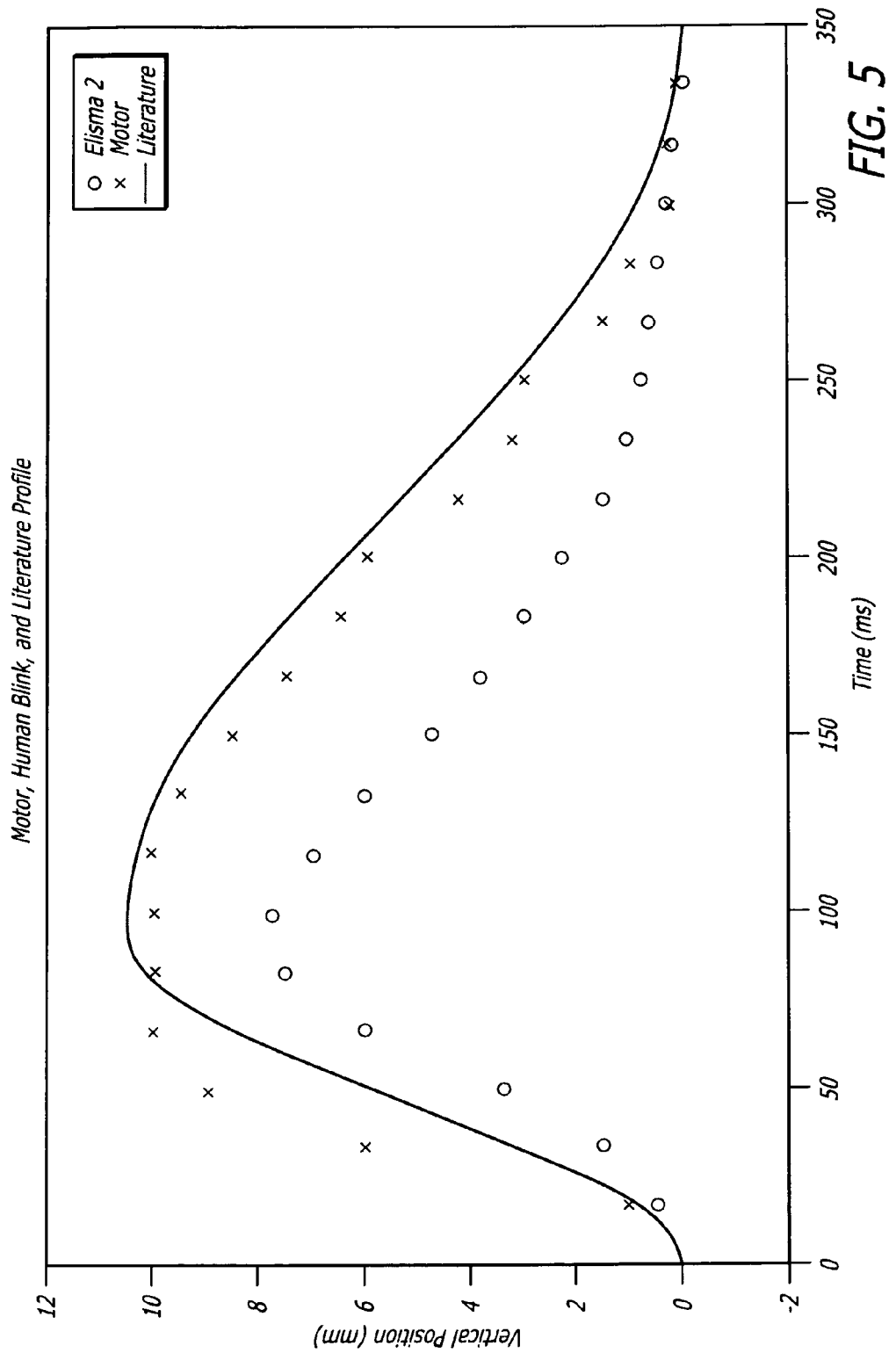
FIG. 5 is the position vs. time profile for the prosthetic eyelid (points identified with an "x"), literature value (solid line), and a human subject's eye blink (points identified with circles).

The position vs. time profile can be seen in FIG. 5. By adjusting the necessary microcontroller script parameters, the position vs. time profile of the prosthetic eye (black points) was matched to the literature profile (blue line) within a 10% error window. The mean percent error for this run was 3.1% with a standard deviation of 2.4%. For reference, a human subject's blink was also recorded (red circles). Though the vertical displacement of the subject's blink profile is different, the overall behavior of the graph is consistent with the literature values. Simple changes can be made in the script to match different blinking profiles, verifying the device's ability to support an adjustable position vs. time profile.

Full Prosthetic Assembly. Assembling the entire prosthetic device is done by attaching the blinking mechanism to the silicone prosthesis (with integrated stainless steel tarsus) according the following instructions.

1. Position the blinking mechanism posterior to the silicone prosthesis such that the front (aesthetic) side of the prosthesis is positioned away from the blinking mechanism.
2. Slide Alignment Hole 240 of Tarsus 200 over the affixed Shaft 500 (not Drive Shaft 110) on the side of Servo Motor 100.
3. Rotate the entire Eyelid 700 by manipulating Tarsus 200 such that the prosthetic eye appears to be open.
4. Align Drive Hole 220 on Tarsus 200 with the threaded hole of Drive Shaft 110.
5. Use one of the small screws provided with Motor 100 to attach Tarsus 200 to Drive Shaft 110 by threading the screw threads through the aligned holes until a tight connection is established.
6. Place precut polyurethane antistatic foam around the blinking mechanism of the device and gently slide the silicone bubble over the foam-supported device. Add more foam as necessary to ensure a snug, padded fit. The device is now ready for patient or model orbital insertion.

The blink characteristics can be modified by altering the script (based on a velocity profile found in the literature) that was loaded onto Servo Controller 300. There are two basic ways that the script can be altered to change the characteristics of the blink: a. Change the duration of time that the eyelid remains closed; or b. Change the speed in which the eyelid opens.

Figure 6:
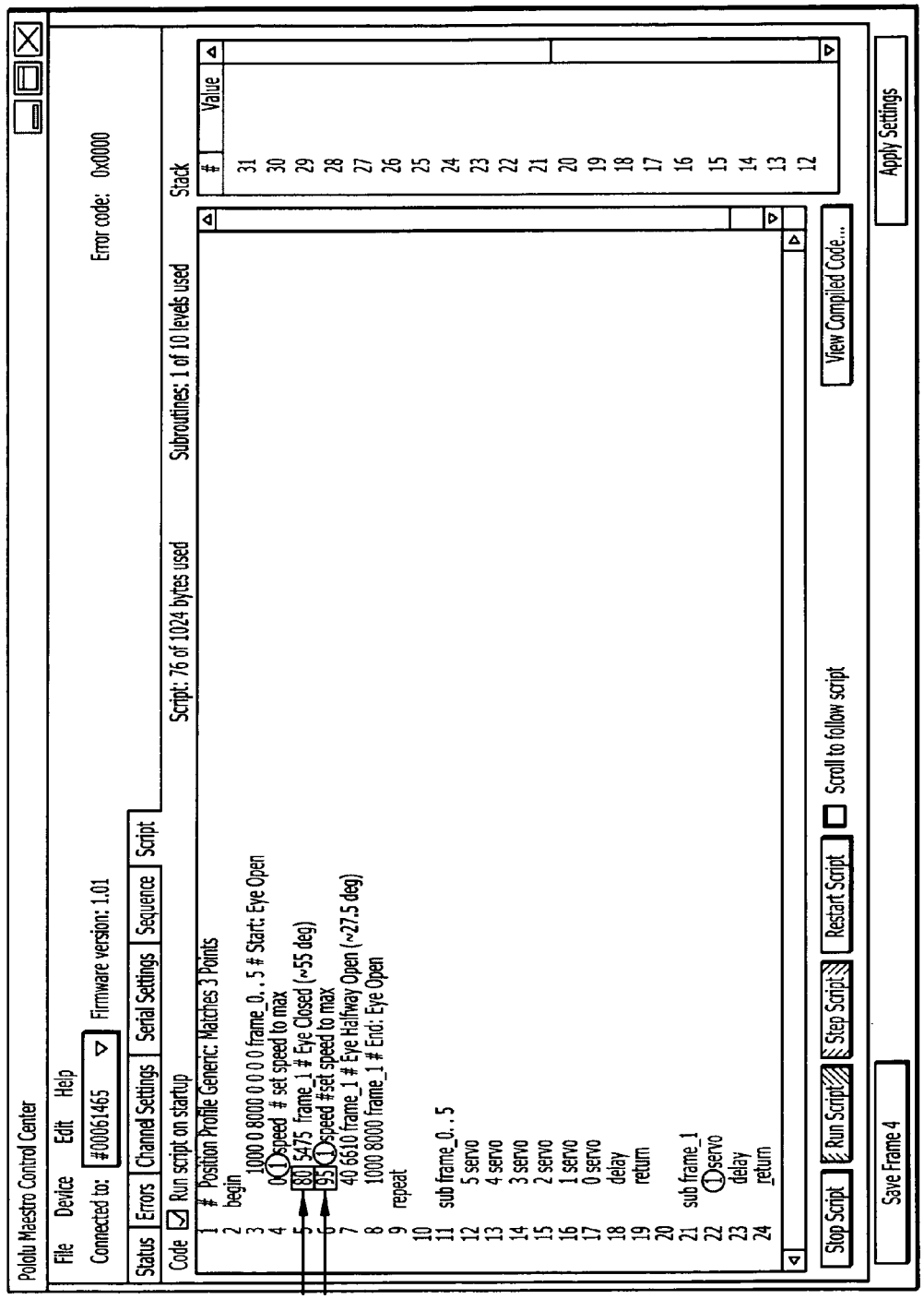
FIG. 6 is the default script loaded onto the microcontroller that matches three critical points in the position profile of the literature reported in vivo human blink.

Referring to FIG. 6, the parameter identified with an arrow, the "80" within the square box, is the duration of eyelid closure (ms), the parameter identified with the second arrow in FIG. 6, the "95" within the rectangular box, is the speed that the eyelid opens, and the numbers circled in yellow are the specified channel designation for the servo motor.

To change the duration of time that the eyelid remains closed, increase or decrease the first value identified with an arrow, the "80" within the square box, in FIG. 6, which corresponds to the desired time value in milliseconds. To change the speed in which the eyelid opens, increase the value identified with the second arrow in FIG. 6, the "95" within the rectangular box, to increase or decrease the speed of Drive Shaft 110. The channel that Motor 100 is controlled through can be changed by altering the "1"s identified in circles in FIG. 6 to the corresponding new channel number. To save any settings that were changed, make sure to press the "Apply Settings" button in the bottom right hand side of the window after making the changes.

A copy of the operation script used to effect an "average" blink is below:

5.29.2013
begin
1000 0 8000 0 0 0 0 frame__0 . . . 5 # Start: Eye Open 0 1 speed # Max Speed
80 6316 frame__1 # Eye Closed
88 1 speed # Slow Motor
40 7334 frame__1 # Eye Halfway open
85 1 speed # Slow Motor more
1000 8000 frame__1 # End: Eye Open
repeat
sub frame__0 . . . 5 5 servo
4 servo
3 servo
2 servo 1 servo 0 servo delay return
sub frame__1 1 servo delay
return Bending the Laser-Cut Tarsus 200. The stainless steel Tarsus 200 can be bent to the appropriate geometry with the help of metal pliers. The side of Tarsus 200 with the slight curvature cut into it is the designated "bottom" or "leading edge" of the eyelid. With this in mind, careful and even bending of the tarsus is accomplished by using two pliers and bending from both sides of Tarsus 200. Position the pliers approximately 10.5 mm in from the edge of the ends of Tarsus 200 and keep these sections straight during the bending process. It can also be helpful to use a curved object to bend around. Once the approximate curvature of Tarsus 200 has been achieved, fine-tuning the curvature is completed by using the acrylic eye and motor shaft attachments as a model.

Attaching Alignment Shaft 500 to Servo Motor 100. The 3D printed Alignment Shaft 500 is positioned on the opposite side of the motor of rotating Drive Shaft 110. To attach Alignment Shaft 500, first mark on Motor 100 where the center of Alignment Shaft 500 will be placed. This point lines up with the center of the threaded hole on rotating Drive Shaft 110. It can be useful to use calipers for help with alignment. It may also be helpful to mark other places on the servo motor to help with aligning the shaft correctly (i.e. where the edges of the shaft should be lined up. Once the alignment has been finalized, use epoxy plastic bonder to affix the Alignment Shaft to the side of the Servo Motor 100 and allow sufficient time for the epoxy to set and cure before use.

We claim:

1. An orbital prosthesis with a natural blink actuation mechanism to recapitulate a natural facial appearance in a human through biomimetic actuation, said natural blink actuation mechanism comprising:

a servo motor comprising a rotatable output shaft on one end and an immobile shaft on an opposite end, wherein the axis of the rotatable output shaft passes through the center of the motor;

a microcontroller functionally coupled to the motor;

a battery functionally coupled to the motor and the microcontroller;

a U-shaped metal tarsus shaped to mimic the human tarsus, said tarsus comprising a first end and a second end, the first end directly coupled to the output shaft and the second end directly coupled to the immobile shaft;

a silicone eyelid bonded to the tarsus;

wherein the tarsus rotates around the motor by rotating about the axis of the rotatable output shaft;

wherein the microcontroller is programmed to rotate the tarsus in a rotational blink motion in both directions, opening and closing of the eyelid, and mimics an in vivo eye blink; and wherein the motor is regulated by pulse width modulation.

2. The mechanism of claim 1, wherein the tarsus is stainless steel.

3. The mechanism of claim 1, wherein the tarsus contains slits.

4. The mechanism of claim 1, where the servo motor provides positional feedback to the microcontroller.

* * * * *